United States Patent
Ntziachristos et al.

(10) Patent No.: US 9,964,747 B2
(45) Date of Patent: May 8, 2018

(54) IMAGING SYSTEM AND METHOD FOR IMAGING AN OBJECT

(75) Inventors: Vasilis Ntziachristos, Gräfelfing (DE); Daniel Razansky, München (DE)

(73) Assignee: Helmholtz Zentrum Munchen Deutsches Forschungszentrum Fur Gesundheit Und Umwelt (GMBH), Neuherberg (DE)

( * ) Notice: Subject to any disclaimer, the term of this patent is extended or adjusted under 35 U.S.C. 154(b) by 692 days.

(21) Appl. No.: 14/406,654

(22) PCT Filed: Jun. 11, 2012

(86) PCT No.: PCT/EP2012/002466
§ 371 (c)(1),
(2), (4) Date: May 7, 2015

(87) PCT Pub. No.: WO2013/185784
PCT Pub. Date: Dec. 19, 2013

(65) Prior Publication Data
US 2015/0247999 A1    Sep. 3, 2015

(51) Int. Cl.
*G02B 21/00*    (2006.01)
*A61B 5/00*    (2006.01)
(Continued)

(52) U.S. Cl.
CPC .......... *G02B 21/008* (2013.01); *A61B 5/0059* (2013.01); *A61B 5/0084* (2013.01);
(Continued)

(58) Field of Classification Search
CPC ........................... G02B 21/008; H04N 5/23229
See application file for complete search history.

(56) References Cited

U.S. PATENT DOCUMENTS 3,013,467 A    12/1961  Minsky
5,062,715 A *  11/1991  Nakata ............... G01N 29/2418
                                                356/432
(Continued)

FOREIGN PATENT DOCUMENTS

JP     06308095 A    11/1994
JP   2003290126 A    10/2003
(Continued)

OTHER PUBLICATIONS

International Search Report and Written Opinion dated May 21, 2013 for PCT/EP2012/002466.
(Continued)

*Primary Examiner* — Shawn An
(74) *Attorney, Agent, or Firm* — Stoel Rives LLP (57) ABSTRACT

An imaging apparatus (100) for imaging an object (1) under investigation, in particular a biological object, comprises a light source device (10) arranged for an illumination of the object (1), a light detector device (20) arranged for detection of light emitted by the object (1) in response to the illumination of the object (1), an acoustic detector device (30) arranged for collecting acoustic signals generated in the object (1) in response to the illumination of the object (1), an image reconstruction device (40) arranged for reconstructing an optical image and an opto-acoustic image of the object (1), and a resolution adaptation device (50) being capable of adjusting imaging properties of the opto-acoustic image, said imaging properties including at least one of the spatial resolution and the imaging depth of the opto-acoustic image. Furthermore, an imaging method for imaging an object (1) under investigation, in particular a biological object, is described.

20 Claims, 5 Drawing Sheets

(51) Int. Cl.
*G01N 29/24* (2006.01)
*G01N 21/17* (2006.01)
*G02B 21/36* (2006.01)
*G01N 29/46* (2006.01)
*G01N 21/64* (2006.01)
*H04N 5/232* (2006.01)

(52) U.S. Cl.
CPC .......... *A61B 5/0095* (2013.01); *A61B 5/6852* (2013.01); *G01N 21/1702* (2013.01); *G01N 21/6458* (2013.01); *G01N 29/2418* (2013.01); *G01N 29/46* (2013.01); *G02B 21/365* (2013.01); *H04N 5/23229* (2013.01)

(56) References Cited

U.S. PATENT DOCUMENTS

| | | | |
|---|---|---|---|
| 8,014,063 B2 | 9/2011 | Sharpe | |
| 8,016,419 B2 | 9/2011 | Zhang et al. | |
| 2003/0090663 A1* | 5/2003 | Autrey | G01N 21/1702 356/432 |
| 2003/0187319 A1 | 10/2003 | Kanoko et al. | |
| 2005/0036667 A1* | 2/2005 | So | G06K 9/00127 382/128 |
| 2007/0015992 A1 | 1/2007 | Filkins et al. | |
| 2007/0109633 A1 | 3/2007 | Stelzer | |
| 2009/0054763 A1* | 2/2009 | Wang | A61B 5/0059 600/425 |
| 2009/0282922 A1* | 11/2009 | Gerstenberg | G01N 29/14 73/606 |
| 2010/0232459 A1* | 9/2010 | Hashimoto | G01J 3/10 372/25 |
| 2010/0249562 A1 | 9/2010 | Zhang et al. | |
| 2011/0231160 A1* | 9/2011 | Suzuki | A61B 5/0059 702/189 |
| 2011/0282192 A1* | 11/2011 | Axelrod | A61B 1/00096 600/427 |
| 2013/0041267 A1* | 2/2013 | Ntziachristos | A61B 1/00009 600/476 |

FOREIGN PATENT DOCUMENTS

| | | |
|---|---|---|
| JP | 2008509713 A | 4/2008 |
| JP | 2011519281 A | 7/2011 |
| JP | 2011193914 A | 10/2011 |
| WO | 2006018686 A1 | 2/2006 |
| WO | 2009055705 A2 | 4/2009 |
| WO | 2011098101 A1 | 8/2011 |

OTHER PUBLICATIONS

Li, et al., "Fast-Scanning Reflection-Mode Integrated Photoacoustic and Optical-Coherence Microscopy", Proceedings of SPIE, 7564(11), Feb. 11, 2010, 75641Z-1 to 75641Z-4.

Ntziachristos, "Going Deeper than Microscopy: The Optical Imaging Frontier in Biology", Nature Methods, 7(8), Jul. 30, 2010, 603-614.

Wang, et al., "Multiscale Photoacoustic Microscopy and Computed Tomography", Nature Photonics, 3(28), Aug. 28, 2009, 503-509.

Yang, et al., "Photoacoustic Tomography: In Vivo Imaging from Organelles to Organs", Science, 335(6075), Mar. 23, 2012, 1460-1461.

Yao, et al., "Photoacoustic Tomography: Fundamentals, Advances and Prospects", Contrast Media & Molecular Imaging, 6(5), Oct. 25, 2011, 332-345.

Zhang, et al., "Collecting Back-Reflected Photons in Photoacoustic Microscopy", Optics Express, 18(2), Jan. 18, 2010, 1278.

* cited by examiner

IMAGING SYSTEM AND METHOD FOR IMAGING AN OBJECT

FIELD OF THE INVENTION

The invention relates to an imaging apparatus and to an imaging method for imaging an object under investigation, in particular a biological object, using optical imaging and opto-acoustic imaging. Applications of the invention are available in imaging techniques, in particular medical imaging.

BACKGROUND

Optical imaging and microscopy has almost four centuries of history with new developments being engineered continuously. Optical imaging operates on contrast mechanisms that offer highly versatile ability to visualize cellular and sub-cellular function and structure of biological objects under investigation. Correspondingly, optical microscopy and imaging are overwhelmingly utilized in biomedical research, for example in immunohistochemistry, in-vitro assays or cellular imaging in-vivo. The compelling advantages of fluorescence are reflected on the recent development of powerful classes of fluorescent tags that can stain functional and molecular processes in-vivo.

A large variety of optical microscopy approaches exist. As an example, in a wide-field fluorescence microscope, the entire specimen is flooded evenly in light from a light source. All parts of the specimen in the optical path are excited at the same time and the resulting fluorescence is detected by the microscope's photo detector or camera including a large unfocused background part, which does not allow three-dimensional imaging. In contrast, advanced methods, such as confocal or multi-photon microscopes, use instead a point illumination to attain three-dimensional tissue sectioning capability. For instance, U.S. Pat. No. 3,013,467 teaches on a confocal microscopy apparatus, which uses a pinhole in an optically conjugate plane in front of the detector to eliminate out-of-focus signal. Multi-photon microscopy achieves a similar effect by selective detection of multi-photon absorption processes occurring in the optical focus. As only light produced by fluorescence very close to the focal plane can be detected, the spatial resolution, particularly in the sample depth direction, is therefore much better for focused methods compared to wide-field microscopes. Since in scattering tissues light can only be focused at a limited depth, microscopic observations are usually limited to specimen or depths of a few tens to a few hundreds of microns.

A major disadvantage of optical microscopy is its dependence on tissue scattering that does not allow imaging beyond a few hundred microns of fully diffusive tissue. This allows only imaging of superficial events that can be misleading and often does not allow interrogation of deeper seated structures. The depth limitations of optical microscopy have shaped entire segments of biology. Even with the advent of confocal and multi-photon tissue sectioning microscopy, only sub-millimeter tissue sections can generally be visualized due to photon scattering by tissue. Imaging deeper in tissue requires the use of (semi-) transparent specimen, i.e only in a few-day old fish or worms. For imaging deeper, the use of implanted windows in mice has been suggested, but even then, only the first few hundred of microns of disease can be visualized.

Optical Projection Tomography (OPT) being the optical analogue to X-ray computed tomography, is a different microscopic method for tomographic imaging of larger objects, which is based on the projection of light through whole transparent specimen.

U.S. Pat. No. 8,014,063 describes an OPT system, which utilizes sample rotation for acquiring transillumination tomographic data. Single plane illumination microscopy (SPIM), described in US 2007/0109633, teaches a similar method, whereby optical sectioning capability is provided by specimen illumination with a thin light sheet. Fluorescence detection is then performed at an angle of 90° relative to the illumination axis.

Larger objects can in principle be imaged with OPT, however the method can be applied in-vivo only to transparent organisms or else to chemically treated specimen to optically "clear" the tissue. This aspect limits the application to mainly fixed specimens as the treatment is toxic. Additionally, the performance of the technique depends on the penetration ability of the chemicals into the tissue and the effectiveness of photon scattering reduction. Similarly to other methods based on optical detection, also SPIM cannot penetrate more than a few hundred microns of fully scattering tissue.

In summary, in current optical microscopy systems and methods the depth that can be achieved is limited. Therefore, in the biological and medical field optical microscopy is limited to superficial tissue investigations only.

Opto-acoustic imaging is a further growing field of imaging techniques that has now seen different implementations, including the multi-spectral optoacoustic tomography approach, which enables imaging based on contrast mechanisms similar to optical microscopy, such as fluorochromes and fluorescent proteins, intrinsic cellular chromophores and extrinsically administered probes and nanoparticles. Opto-acoustic imaging has demonstrated powerful performance in imaging of optical contrast deep within several centimeters of living tissues. This is because opto-acoustics can visualize optical absorption with resolution that is not affected by photon scattering. Instead, optical contrast and markers are visualized with ultrasonic resolution. Using advanced illumination systems, high frequency detectors, and reconstruction methods, the currently achieved opto-acoustic imaging quality has already shown high potential for high-resolution imaging within several millimeters of fully scattering tissue.

Opto-acoustic imaging is insensitive to tissue scattering and can extend the application regime of optical microscopy deeper in tissues with relatively high (mesoscopic) resolution. Yet, despite significant progress, the current mesoscopic opto-acoustic imaging implementations are still limited in terms of achievable spatial resolution. Therefore, specimen of less than 5 to 7 mm in diameter could not be imaged with good image quality. Scanning times could reach an hour or more for three-dimensional imaging. Sample placement required experience and was complicated by insufficient holders. Also no optical view of the specimen was available during scanning, which further complicated specimen placement.

Zhang et al. ("Opt. Express" vol. 18, 2010, p. 1278-1282, U.S. Pat. No. 8,016,419 B2, and US 2010/0249562 A1) have proposed a combination of confocal microscopy and opto-acoustic imaging. According to Zhang et al., both of an optical image and an opto-acoustic image of an object are reconstructed. The optical image is collected with a confocal microscopy set-up, while the opto-acoustic image is collected with a single detector element or a detector array. The confocal microscopy set-up inherently requires a focussed illumination of the object. Due to the scattering properties of biological objects, the focussed illumination is restricted to the surface section of the object. The opto-acoustic image obtained by Zhang et al. is restricted to the surface section of the object, as well. The opto-acoustic image is restricted to the region, where the focussed illumination is provided.

OBJECTIVE OF THE INVENTION

The objective of the invention is to provide an improved imaging apparatus and an improved imaging method being capable of avoiding limitations of conventional imaging techniques. In particular, the objective of the invention is to provide an improved imaging technique allowing an imaging beyond the penetration limits of optical microscopy and/or avoiding a limitation of the opto-acoustic imaging to a certain surface section of the object under investigation.

SUMMARY OF THE INVENTION

These objectives are solved by the imaging apparatus and the imaging method comprising the features of the independent claims. Advantageous embodiments and applications of the invention are defined in the dependent claims.

According to a first aspect of the invention, an imaging apparatus for imaging an object under investigation, in particular a biological object, is proposed, which comprises a light source device including at least one light source arranged for an illumination of the object, a light detector device arranged for detection of light created, e. g. emitted, reflected and/or scattered) at the object in response to the illumination thereof, an acoustic detector device arranged for collecting acoustic signals generated in the object in response to the illumination thereof, and an image reconstruction device arranged for reconstructing both of an optical image and an opto-acoustic image of the object. The spatial resolution of the optical image depends upon characteristics of the optical system, i.e. the light source device, the light detector device and/or an optical imaging device. In particular, the resolution in optical microscopy is typically dependent on the optics of the optical imaging device and/or the light source device employed; i.e the numerical aperture of the lens, geometrical characteristics and the wavelength employed. The spatial resolution of the opto-acoustic image depends upon characteristics of at least one of the illumination system, the acoustic detection system and/or the geometric arrangement of the acoustic detection system. In particular, in opto-acoustic imaging, the resolution can be adapted by the ultrasonic frequency component employed. As an example, detectors of different frequencies could be employed. Generally, according to the invention, the imaging apparatus comprises a resolution adaptation device which is adapted for adjusting imaging properties of the opto-acoustic image, wherein the imaging properties include the spatial resolution and/or the imaging depth of the opto-acoustic image.

According to a second aspect of the invention, an imaging method for imaging an object under investigation, in particular a biological object, is proposed, which includes the steps of illuminating of the object with a light source device, detecting light emitted by the object in response to the illumination thereof, collecting acoustic signals generated in the object in response to the illumination thereof, and reconstructing both of an optical image and an opto-acoustic image of the object. According to the invention, the imaging method further comprises a step of adjusting imaging properties of the opto-acoustic image which include the spatial resolution and/or the imaging depth of the opto-acoustic image. Preferably, the imaging method of the invention is implemented with the imaging apparatus according to the above first aspect of the invention.

In particular, the invention is based on the approach to provide a hybrid optical and opto-acoustic imaging apparatus and method being configured both for optical imaging, preferably microscopic optical imaging of, in particular biological, objects, and opto-acoustic imaging of the objects. In particular, microscopic optical images of the objects can be obtained within the penetration limits of optical microscopy with a high resolution of typically below few microns. Moreover, opto-acoustic images with lower resolution of typically a few microns to a few tens of microns can be obtained from regions of the objects beyond the penetration limits of optical microscopy. Because the typical resolution of opto-acoustic imaging is between the resolution of optical microscopic imaging on the one hand and macroscopic structures which can be seen with the human eye on the other hand, the typical resolution achieved by opto-acoustic imaging is also referred to as mesoscopic resolution.

The current invention therefore provides a combination of (microscopic) optical and opto-acoustic imaging that defines a new imaging regime by which a new class of images are collected. A particularly important feature of the invention is that ultrasound-diffraction-limited images can be produced as an addition to optical images, extending the applicability of the hybrid system to specimen or depths of dimensions not accessible by optical microscopy techniques. A further important aspect of the invention is that images of varying resolution with depth can be produced; preferably by optimally interfacing, i.e. adapting, the characteristics of the hybrid system to the desired imaging depth. In this manner, optical resolution can be gradually exchanged for high-frequency opto-acoustic resolution, which will further reduce at large depths or specimen volumes according to physical principles of ultrasound propagation in tissues (diffraction, refraction, dispersion). This approach can be employed to combine many diverse features on the images produced, such as high-resolution cellular imaging and corresponding host tissue visualization at depths >1 mm, visualization of natural contrast and induced contrast, for example fluorescence or nano-particles and three-dimensional cell tracking applications deep in scattering tissues.

In particular, the invention utilizes opto-acoustic principles, implemented together with optical imaging, in order to offer a highly versatile system capable of imaging diverse optical contrast at multiple wavelengths (absorption, fluorescence) and the ability to provide high-resolution imaging beyond the depth allowed by current optical microscopy methods.

Another important aspect of the invention is that the same contrast can be visualized through the resolution and depth scaling of the imaging methods considered. This can be achieved by employing multi-spectral opto-acoustic tomography principles which can resolve the same photo-absorbing moieties imaged also by optical imaging, for example the same fluorochrome. Therefore, images of varying resolution and depth but of the same contrast can be achieved. In addition the hybrid method can superimpose also contrast unique to each modality considered in the hybrid implementation, such as fluorescence images coming from the optical method with nano-particle or blood vessel images coming from the opto-acoustic method.

The invention does not only significantly improve on penetration depths of optical microscopy but can also adapt the resolution with depth, spanning from specimen of a few hundred microns in depth (diameter) and a few microns resolution to specimen of ~5 mm in diameter and <30 μm resolution by adapting the frequency range employed from broadband transducers, i.e. adapting the so-called frequency response of the acoustic detector device, or even utilizing different acoustic sensors for the different frequencies considered. Opto-acoustic imaging allows for imaging of optical contrast deep within several centimeters of living tissues. This is because opto-acoustics can visualize optical absorption with resolution that is not affected by photon scattering. Instead, optical contrast and markers are visualized with ultrasonic resolution. For instance, a whole body cross-sectional imaging of small animals, such as adult mice, is possible. Using advanced illumination systems, high frequency detectors and reconstruction methods, the achieved opto-acoustic imaging quality yields mesoscopic resolution imaging within several millimeters of fully scattering tissue. As opto-acoustic imaging is insensitive to tissue scattering, it can extend the application regime of optical microscopy deeper into tissues with a relatively high, i.e. mesoscopic, resolution.

The terms "mesoscopic imaging" and "mesoscopy" imply that the spatial resolution of the opto-acoustic images obtained by the hybrid optical/opto-acoustic method and apparatus is established by the diffraction-limited resolution of the at least one ultrasonic detector of the acoustic detector device, said resolution being typically in the range of a few microns (µm) to a few tens of microns (µm). This generally results in reduced resolution compared to diffraction-limited optical approaches in scattering-free specimen (depth) or in scattering media assuming cross-sectional microscopy methods such as confocal or two-photon microscopy, yet significantly better than in the case of macroscopic optical tomography, for example Fluorescence Molecular Tomography applied to deep-tissue imaging in diffuse specimen.

Contrary to the imaging technique of Zhang et al., where the resolution is determined by the diffraction-limited optical focus while the imaging depth is limited by the optical focusing ability in scattering tissues to about few hundreds of µm, the spatial resolution and/or the imaging depth adjustment of the opto-acoustic imaging as proposed by the current invention allows to accomodate the imaging system to the object under investigation. As a result, the invention allows to extend the imaging depth of optical microscopy to a deeper mesoscopic regime in an "all-in-one" imaging system and method and offers, therefore, a varying resolution spanning from optical resolution in superficial microscopic imaging to ultrasonic resolution in opto-acoustic imaging in higher depths within the tissue.

In preferred embodiments of the invention, the acoustic detector device is arranged such that the spatial resolution of the opto-acoustic image of the object is determined by characteristics of the acoustic detector device, in particular by a spatial configuration, a frequency response and/or a movement of the acoustic detector device. By these means, a spatial resolution and/or penetration depths of the opto-acoustic image can be achieved independently from the properties of the optical imaging device. Spatial configurations of the acoustic detector device may be, e.g., a shape of one or more sensitive surfaces of the acoustic detector device and/or a spatial arrangement of one or more acoustic detector devices relative to the object under investigation. Additionally or alternatively, the spatial resolution of the opto-acoustic image may also be determined by the frequency response of the acoustic detector, wherein signals produced by the acoustic detector depend on the frequency of the detected sound and/or ultrasound waves. Preferably, the acoustic detectors should have ultrawideband response so an accurate shape of the detected optoacoustic signals is preserved by broadband detection from e.g. several MHz up to several tens of MHz. Additionally or alternatively, the spatial resolution of the opto-acoustic image can also be constituted by a movement of the acoustic detector relative to the object under investigation.

Advantageously, multiple variants of the resolution adaptation device exist, which can be implemented alone or in combination.

Thus, according to a preferred embodiment of the invention, the resolution adaptation device includes a filtering unit arranged for subjecting the collected acoustic signals to at least one frequency filtering selected in dependency on the imaging properties to be obtained. Advantageously, at least one of the following filtering modes can be provided. Acoustic signals having high frequencies, e. g. in the range from 30 MHz to 60 MHz are transmitted to the image reconstruction device if the opto-acoustic image is to be collected with high resolution (15 µm to 30 µm) and low imaging depth of several mm within the object. Alternatively, acoustic signals having low frequencies, e. g. in the range from 5 MHz to 10 MHz, are transmitted to the image reconstruction device if the opto-acoustic image is to be collected with low resolution (100 µm to 200 µm) and large imaging depth of 1 cm and more within the object. Thus, the filtering unit provides the resolution adjustment of the invention. Particularly preferred, the filtering unit is arranged for subjecting the collected optoacoustic signals to a wavelet-domain filtering to perform multiresolution analysis and simultaneously achieve opto-acoustic images with scalable resolution and depth.

According to a further preferred embodiment of the invention, the resolution adaptation device includes a drive unit being arranged for moving the acoustic detector device or parts thereof relative to the object. As an example, the acoustic detector device may comprise one single or multiple detector element(s) being movable relative to the object. Alternatively, the drive unit can be arranged for moving the at least one detector element along a linear or curved, in particular a circular line, and/or along a planar or curved surface, in particular a cylindrical or spherical surface. Thus, with a preferred variant of the invention, the acoustic detector device comprises at least one detector element being movable or moved relative to the object under investigation. Although only one or a few detector elements are provided, mesoscopic opto-acoustic images of high quality can be obtained in this way.

According to a yet further preferred embodiment of the invention, the resolution adaptation device includes a light source modulation unit arranged for subjecting the illumination of the object to a predetermined input modulation selected in dependency on the imaging properties of the opto-acoustic image to be obtained. Particularly preferred, the input modulation includes at least one of frequency modulation, in particular chirp modulation, amplitude modulation, phase modulation and digital modulation. As preferred examples, the input modulation may include at least one of a linear, logarithmic, sin-like, square-like, and triangle-like frequency modulation. According to a particularly preferred aspect of the invention, the illumination device has at least an intensity varying element in order to generate an opto-acoustic response. To this end, the light source device may include optical reflective and/or refractive components, like mirrors, galvanometers or other moving parts and lenses.

According to a yet further preferred embodiment of the invention, the resolution adaptation device includes a light source scanning unit arranged for applying a scan pattern to the illumination of the object, and/or a switching unit arranged for switching between optical resolution and optoacoustic resolution, e.g. by adapting the illumination from focused to less focused to wide-beam; and then instead using acoustic resolution.

Further advantages in terms of adjusting the resolution of the opto-acoustic image can be obtained if the acoustic detector device is arranged for collecting the acoustic signals along a plurality of angular projection directions (view angles) through the object. Advantageously, by arranging the ultrasonic detectors to obtain opto-acoustic signals from different projections (view angles) from the sample, and in particular the combination with tomographic methods, high-resolution images can be obtained. In its simplest form, opto-acoustic images can be obtained by scanning a spherically-focused detector along the imaged object and image formation using a delay-and-sum algorithm. Alternatively, according to a particularly preferred embodiment of the invention, the acoustic detector device comprises a detector array with multiple detector elements being distributed in proximity to the object, in particular around the object. According to this embodiment, mesoscopic opto-acoustic imaging beyond the typical microscopic penetration depths is enabled in an easy and reliable manner.

Furthermore, the multiple detector elements can be located on at least one of a linear or curved, in particular a circular, line and a planar or curved surface, in particular a cylindrical or spherical surface, around the object. By this means, mesoscopic opto-acoustic imaging beyond the typical microscopic penetration depths is enabled in an easy and reliable manner.

Preferably, the mesoscopic imaging device comprises ultrasonic detection from multiple positions and orientations in response to an illumination pattern. To achieve multiple position detection, the detector array can be used, the single acoustic detector scanned at multiple positions or a combination of an array and a scanning scheme. Respectively, the light source device can be stationary or be scanned and/or the object under investigation can be moved or be stationary.

According to another advantageous feature of the invention, the acoustic detector device may comprise at least one unfocussed detector element by means of which volumetric opto-acoustic image information of the object is obtained. By the unfocussed detector element sound and/or ultrasound waves can be detected, which are generated in a larger volume of the object as compared to the wave that can be detected by a focussed detector. By this means, more accurate volumetric opto-acoustic image information can be obtained in a tomographic fashion.

Alternatively or additionally, the acoustic detector device comprises at least one focussed, in particular spherically or cylindrically focussed, detector element by means of which opto-acoustic image information is obtained simultaneously from locations on a line or plane on or within the object. Preferably, the spherically focussed detector element is arranged for detecting acoustic waves emitted from small, e.g. point-like, circularly or elliptically shaped regions on or within the object and/or comprises a spherically shaped sensitive detector surface. A cylindrically focussed detector element is arranged for detecting acoustic waves emitted from linearly shaped regions on or within the object and preferably comprises a cylindrically shaped sensitive detector surface. By this means, high-quality opto-acoustic images can be obtained from specifically selectable locations, in particular points, lines and/or planes, respectively, on or within the object in an easy and reliable manner. Alternatively, the imaged object can be rotated while the acoustic detector remains stationary. This particular embodiment might be convenient when combining opto-acoustic tomography with, e.g., optical projection tomography (OPT) or mesoscopic fluorescence tomography, in which sample rotation is usually essential. Accordingly, with a particularly preferred embodiment of the invention, the image processing device is configured for creating a tomographic opto-acoustic image of the object with the ultrasound spatial resolution.

Particularly preferred, the acoustic detector device comprises a detector array with multiple focussed detector elements. The detector elements are located along predetermined locations in space, for example a two dimensional pattern, a reference line such as a circle or a cylindrical or spherical surface. Hybrid implementations of a combination of two-dimensional surfaces may also bring certain imaging benefits. Accordingly, the detector elements are in this manner be distributed around the object. Depending on the application of the invention, the detector elements can be arranged on a surface of the object or on a carrier device, such as cylindrical or circular or other carrier. Using multiple detector elements has an advantage in terms of simultaneous collection of opto-acoustic data, e.g. for achieving real-time opto-acoustic tomographic images.

Alternatively, the acoustic detector device may comprise at least one detector element, which is movable with respect to the object. This embodiment can have advantages in terms of an optimal adaptation of the detection points' location relative to the object for optimal tomographic data collection. The at least one detector element can be moved, e.g. translated and/or rotated, along a certain reference surface.

According to a further preferred embodiment of the invention, image reconstruction device is arranged for reconstructing different portions (sections, segments) of the object. Preferably, the optical image can be or is obtained from the first segment of the object and the opto-acoustic image can be or is obtained from the at least one second segment of the object. The first segment (superficial segment, surface segment) of the object is located at the surface or near the surface of the object, while the at least one second segment (volume segment) of the object is extended within the object, i.e. at a finite distance from the surface of the object. However, the second segment may include the first segment. With imaging the at least one two segments, two images are obtained, namely one optical image, in particular an optical microscopic image, from the superficial segment of the object with optical resolution and one mesoscopic opto-acoustic image from at least one second segment located within the object and preferably adjoining or including the captured optical image from the superficial segment. By combining the captured optical and opto-acoustical image information, a hybrid optical/opto-acoustic image can be obtained, wherein a first part of the hybrid optical/opto-acoustic image only contains an optical image and a second part of the hybrid optical/opto-acoustic image only contains an opto-acoustic image of the object.

In a particularly preferred configuration of this embodiment, the opto-acoustic image can be obtained from the first and the second segment of the object. With this configuration, a first optical image, in particular an optical microscopic image from a superficial segment of the object with optical resolution, is obtained, and a second mesoscopic opto-acoustic image from both the superficial segment and the segment located within the object is obtained. Accordingly, the first part of a combined hybrid optical/opto-acoustic image contains both an optical image and an opto-acoustic image of the object and a second part of the hybrid optical/opto-acoustic image only contains an opto-acoustic image of the object.

According to a preferred embodiment of the invention, the resolution adaptation is implemented for adjusting the opto-acoustic imaging of the at least one second segment in dependency on optical, acoustic and/or geometric properties of the object or parts thereof.

In further preferred embodiments of the invention the light source device is adapted for at least one of a wide-field illumination of the object, a patterned illumination of the object, in particular by scanning a pattern on the object, a single plane illumination of the object, a focused illumination of the object, in particular by scanning a light focus on the object, a pencil-beam illumination of the object, an illumination of the object with a varying light intensity, in particular a pulsed illumination, and an illumination of the object at two or more different wavelengths. With the wide-field illumination, a surface region of the object covering a region of investigation is homogeneously illuminated. Correspondingly, the patterned or the focused illumination yields a patterned or focused light field distribution on the surface region of the object, which can be time-varying, e.g. by scanning the pattern or light focus. Planar illumination shows benefits in mesoscopic opto-acoustic imaging by selecting a narrowly defined volume or a thin slice illuminated.

Furthermore, by varying the light intensity of the illumination of the object corresponding acoustical waves are emitted from the object, which can be detected by the acoustic detector device. Preferably, the time variation of the light intensity is chosen so that, in response to the variable illumination, acoustic waves are generated which can be efficiently detected by the acoustic detector. Preferably, the light intensity can be varied so that periodic pulses are obtained. It is, moreover, possible to illuminate the object at two or more different wavelengths in order to obtain images or information relating to different photon excitation/absorption properties of the object, e.g. due to the presence of biomarkers. Preferred realizations and particular advantages of different illumination profiles and shapes, i.e. wide-field, patterned, single-plane, focused and pencil-beam, will be set forth below in detail. Preferably, the light source device includes at least one light-emitting diode, at least one laser diode, and/or at least one pulse laser source. The pulse laser source preferably is adapted for creating illumination light which can be absorbed in the object by multi-photon absorption.

According to a further advantageous embodiment of the invention, the imaging apparatus includes an imaging device, preferably microscope device, which is configured for projecting the light emitted by the object onto the light detector device. Preferably, the imaging device is an optical microscope. The microscope may comprise an objective lens, an ocular and an optical system for sample illumination. Preferably, the optical microscope is a confocal and/or multi-photon laser scanning microscope. Combining the opto-acoustic imaging device according to the invention with an optical microscope of this type considerably extends the imaging range of the system beyond the penetration limits of optical microscopy. In particular, when the acoustic detector device is arranged such that the spatial resolution of the opto-acoustic image of the object is determined by the characteristics of the acoustic detector device, the resolution of the mesoscopic opto-acoustic images is not limited by the optical microscope device and can therefore be chosen separately and adequately.

A potent combination is the use of confocal or two-photon laser scanning microscopy into the hybrid system. Confocal and two-photon microscopy can also very accurately select a slice illuminated. In this case, imaging with a multitude of acoustic detectors, as proposed with the inventive system herein, can even lead to optical resolution opto-acoustic microscopy with increased signal to noise ratio. This is because multiple acoustic transducers detect signals from the same volume illuminated by the laser scanning microscopic technique. Increased signal to noise ratio can lead not only to opto-acoustic absorption imaging (i.e. imaging blood vessels) and multi-spectral imaging (i.e. imaging photo-absorbing molecules), but also to two-photon absorption opto-acoustic imaging. This is a particularly synergistic effect of the hybrid system proposed, especially when an ultrasonic array is employed. A further advantage of the combination with confocal or two-/multi-photon microscopy and the mesoscopic opto-acoustic method is that the depth that is achieved by two-photon (or confocal) microscopy is generally deeper than other microscopy methods. This allows a more seamless transition from microscopic to mesoscopic imaging regimes.

According to a particularly preferred and advantageous aspect of the invention, the light source device, the light detector device and the acoustic detector device are coupled with an endoscope device. Preferably, the acoustic detector device is arranged or provided on a distal portion of the endoscope device. The acoustic detector device may comprise piezo-electric detection element/s or detection elements based on optical interferometry, e.g. Fabry Perot layers or fiber-based Bragg gratings. Alternatively or additionally, it is preferred that the light source device and/or the light detector device is/are arranged or provided on a proximal portion of the endoscope device. These embodiments allow for a highly compact setup and, therefore, a reliable minimal-invasive medical examination, in particular of a living human or animal body, by using the inventive system and method.

Further advantageous features of the invention are summarized in the following.

The light source device may include optical reflective and/or refractive components, like mirrors, galvanometers or other moving parts and lenses. The light source device can also be considered having multiple wavelengths. The light detector device, like e.g. a photodetector or a CCD detector, is arranged for collecting light signals created in the object after an input of the illumination light. Thus, the light detector device, preferably including spectral filtering components, can be adapted for collecting, e.g., scattering, reflection, absorption and/or fluorescence light emitted by the object under investigation. The light can be projected by means of a lens, for example a compound microscopy system, onto the light detector device.

Furthermore, the hybrid optical/opto-acoustic imaging system includes an opto-acoustic imaging device having an acoustic detector device being arranged for collecting acoustic signals created in the object in response to the illumination of the object by said light source device and/or additional light source dedicated for a generation of acoustic signals emitted by the illuminated object. The acoustic signals collected with the acoustic device can be generated in response to the same illumination light source device as to the one used for data collection by the optical microscope, or different illumination light source devices applied simultaneously or in a time shared manner.

The acoustic detector device is preferably adapted and/or arranged in relation to the light source device and/or optical imaging device in such a way that the acoustic detector device does not interfere, i.e. block, the optical illumination and detection path and, vice versa, the optical imaging device does not interfere, i.e. block, the acoustic detection path.

The hybrid optical/opto-acoustic imaging system of the invention includes an image reconstruction device being arranged for processing the light signals and the acoustic signals and for generating optical, opto-acoustic and/or optical/opto-acoustic hybrid images, i.e. combined optical and opto-acoustic images of the object. Advantageously, the optical image can be employed to guide the specimen placement for opto-acoustic imaging. In addition, a hybrid image can be created on the basis of optical image data and opto-acoustic image data, wherein hybrid image data are reconstructed from both the light signals and the acoustic signals.

Illumination plays an important role in the implementation of the hybrid system according to the invention. While the system can be geometrically matched due to a common reference point (or multiple points), the matching of the optical contrast visualized is of importance. Of particular importance for mesoscopic opto-acoustic imaging is the illumination at multiple wavelengths so that through multi-spectral un-mixing techniques imaging of different photo-absorbing molecules can be achieved. Although any number of wavelengths can be used (for example, even the use of two wavelengths can reveal spectral differences), the accuracy of resolving different photo-absorbing molecules significantly improves when more than two wavelengths are used. Preferably, the number of wavelengths should be approximately at least twice the number of photo-absorbing moieties to be resolved for the first few photo-absorbing moieties. In this manner, a large number of photo-absorbing moieties can be determined. Characteristically, imaging of fluorescent proteins, fluorescent and absorbing dyes, targeted fluorochromes, oxy- vs. deoxy-hemoglobin, transgenic cells expressing molecules that generate optical contrast (for example beta-gal, melanin) and nanoparticles (gold, carbon, labelled or loaded liposomes) and many others.

Contrast combination is another powerful synergistic effect of the hybrid system according to the invention. Even at varying resolution, photo-absorbing moieties can be tracked at significantly larger volumes (deeper) than the ones allowed by conventional microscopy.

Geometrical arrangement of the illuminating sources also plays a vital role in order to achieve even more advantages of the invention. Typically, broad-field (non-focused) illumination can be applied from different directions onto the object in order to improve homogeneity of light distribution in the object. A preferred embodiment illuminates the object through the objective used for microscopy. However, for larger specimen which are not fully accessible from one direction more than one illumination paths may exist, to more evenly illuminate the object from multiple projections. Moreover, more than one illumination type can be combined, depending on the particular imaging performance characteristics required. The direction of the illumination could be established from one side of the object, in particular when specimens of only a few mm are considered. Since photons undergo significant scattering and absorption in most tissues, the reconstructed images can be corrected for light attenuation using numerical simulations based on, e.g., light transport or Monte-Carlo equations or blind decomposition approaches.

Focused and broad field illumination can be also combined. Since different moieties and different light illumination technologies can generate different signals, there are several ways of multiplexing light sources. For example, light of varying intensity (for opto-acoustic generation) can be simultaneously combined with light of constant intensity (for example for fluorescence imaging). In addition, light of different wavelengths can be combined simultaneously or in a time shared fashion. Simultaneous illumination at different wavelengths can also make use of intensity varying instead of intensity invariant illuminations. Moreover, it can be made use of different established contrast mechanisms, e.g. an absorber and a fluorochrome are both present with no overlapping spectral contributions. For instance, imaging blood vessels with opto-acoustics in the 600 nm region can be done together with imaging fluorescence in the 800 nm region. An important synergy effect when simultaneous optical imaging is applied is the imaging acceleration since data can be acquired in parallel.

According to a further inventive aspect of the hybrid system the utilization of broad-band detector elements is provided. By dynamically selecting the desired frequency band, the appropriate resolution and penetration depth can be established. This Dynamic Resolution Adaptation (DRA) allows optimally adapting characteristics of the system to the volume sample (depth) desired. To achieve this, preferably Fourier domain filtering can be applied to the raw opto-acoustic signals or the reconstructed images. Alternatively, multiresolution approaches, such as wavelet-domain filtering can be done to optimally accommodate for the ultra-wideband nature of typical opto-acoustic signals.

Correction for out-of-focus artifacts and image blurring can be further achieved by applying a virtual detector approach or other methods that can deconvolve the effects of the detector's spatial response from the image. When applying two- or three-dimensional tomographic scanning by, e.g., a cylindrically-focused or unfocused detector, images can be readily obtained by explicitly formulated approximated back-projection (so-called Radon-based) inversion methods.

The approximate back-projection formulas are widely used mainly due to their simplicity and are generally convenient and fast but not exact and may—in some cases or applications—lead to the appearance of substantial artifacts in the reconstructed images. A common problem is suppression of slowly varying image components and accentuation of fast changes in the image (small details), which is usually also accompanied by negative optical-absorption values that otherwise have no physical interpretation. In addition, back-projection algorithms are based on an ideal description of the acoustic wave propagation and detection as well as on specific detection geometries, therefore they cannot be easily generalized into a more realistic opto-acoustic illumination-detection models that incorporate configuration and instrumentation-dependent factors.

Preferably, back-projection-related artifacts can be avoided by use of the so-called model-based inverse methods. These methods calculate numerically a propagation of opto-acoustically-generated waves in tissues using the Poisson-type integral, which provides expression for the integrated pressure wave p($\vec{r}$',t) sensed by acoustic detector located at $\vec{r}$', given via a Poisson-type integral $$p(\vec{r}\,',t) = \frac{\beta}{4\pi v_s^2 C}\frac{\partial}{\partial t}\int_{R=v_s t}\frac{H_r(\vec{r})}{R}dA, \quad (1)$$

where $R=|r-r'|$, $H_r(\vec{r})$ is the absorbed energy density, $v_s$, $\beta$, and C are the corresponding speed of sound, isobaric volume expansion, and specific heat coefficients of the medium. For each time point t, the spatial integration is performed over a spherical shell with a radius of $R=v_s t$.

This formulation is valid when assuming that duration of the optical excitation pulse is short enough to be approximated by a delta function, which is true in many practical cases.

In contrast to back-projection algorithms, model-based schemes are therefore not based on an approximate analytical solution of the opto-acoustic equation. Instead, the forward problem is solved numerically in an iterative optimization algorithm. In each iteration, the reconstructed opto-acoustic image is changed to reduce the error between its corresponding acoustic signals and the measured signals.

Preferably, by using numerically efficient interpolated-model matrix inversion (IMMI), these methods are not faced with long computation times. IMMI solves Eq. (1) in a highly efficient semi-analytical manner by applying linear interpolation to $H_r(\vec{r})$ and performing the integral analytically. This leads to a discretization of Eq. (1), given by the following matrix relation:

$$p = Mz \quad (2)$$

where p represents pressure fields measured at different positions (projections), z are values of opto-acoustic image on the defined grid, and M is the acoustic forward-model matrix.

The opto-acoustic image is obtained by inverting Eq. (2). Two common methods are the Moore-Penrose pseudo-inverse and the least-squares decomposition (LSQR) algorithm. The pseudo-inverse of M is given by $$M^+ = (M^H M)^{-1} M^H, \quad (3)$$

while the reconstructed opto-acoustic image is subsequently obtained via $$z = M^+ p. \quad (4)$$

The main advantage of using the pseudo-inverse is that it needs to be calculated for a given system only once, allowing for very fast inversion, which can in principle be done in real time. On the other hand, LSQR is an iterative algorithm for solving linear equations. Its main advantage is high efficiency in the case of sparse matrices. In addition, LSQR requires saving only the nonzero elements of the matrix, thus mitigating memory requirements. Since the model matrix M is sparse, LSQR is an extremely efficient method for inverting Eq. (2) when the number of grid points is high.

Model based methods can further incorporate the detector functional characteristics, such as the impulse response, to yield even more accurate image quality. Further synergistic effects can be achieved by combining optical and opto-acoustic information. For example, information on optical properties from optical microscopy can be employed to model light attenuation as a function of depth, which can be employed in opto-acoustic imaging. Preferably, in the image formation process, especially in high resolution opto-acoustic mesoscopic imaging, a correction for frequency-dependent sound attenuation (dispersion) is performed. As attenuation is frequency dependent, such a correction can be done on a per frequency basis.

The inventive resolution adaptation potentially can be sensitive to ultrasonic attenuation correction. For frequencies above 40 MHz in particular, ultrasonic attenuation can determine the maximum depth achieved and frequency dependent attenuation correction becomes necessary for quantitative imaging.

According to another particularly preferred embodiment of the invention, the image processing device is configured for creating not only a hybrid image, but also at least one of an optical image and an opto-acoustic image. In particular, the optical image has the advantage that the arrangement of the acoustic detector device can be done under optical control, i.e. the acoustic detector device can be positioned relative to the object in dependency on optical image data collected from the object. As a further advantage, the optical image data and/or the opto-acoustic image data can be used for reconstructing the opto-acoustic image and the optical image, respectively, and vice versa.

Generally, the object to be imaged may comprise, e.g., a human or animal subject, or a part thereof, or non-biological matter, like an inner space of a chemical reactor or the like. For medical imaging, the hybrid opto-acoustic mesoscope device can be coupled with an endoscope device. Thus, the light source device, the light detector device and the acoustic detector device are coupled with the endoscope device. Preferably, the acoustic detector device is arranged on a distal portion of the endoscope device, so that hybrid or opto-acoustic images can be collected representing an inner portion of the object investigated.

Preferably, in the opto-acoustic imaging method according to the invention a multi-spectral opto-acoustic tomography (MSOT) approach is applied, which enables highly sensitive imaging based on contrast mechanisms similar to optical microscopy, such as fluorochromes and fluorescent proteins, intrinsic cellular chromophores and extrinsically administered probes and nanoparticles. In many cases, depending on their concentration, contributions of various photo-absorbing agents, such as contrast agents, targeted probes or nanoparticles may constitute only small signal variances over the background absorption. This may complicate detection of the photo-absorbing agent on single wavelength images, even if the selected wavelength corresponds to the absorption maximum of the agent of interest. When data at multiple wavelengths are obtained however, it is possible to improve the contrast and detection sensitivity by spectral unmixing, i.e. by resolving the spectral signature of the absorber agent used over other non-specific spectral contributions, e. g. from highly absorbing hemoglobin.

Spectral unmixing methods based on differential or fitting algorithms use the known spectral information to process the image on a pixel-by-pixel basis. Those methods try to find the source component (e.g. a distribution of a certain contrast agent) that best fits its known absorption spectrum in the least-squares sense.

Given the (n×m) multispectral measurement matrix M, where n is the number of image pixels and m is the number of measurements, as well as the (k×m) spectral matrix S with the absorption coefficients of the k components at the m measurement wavelengths, the data can be unmixed via $$R_{pinv} = MS^+, \quad (5)$$

where $S^+$ is the Moore-Penrose pseudoinverse of S and $R_{pinv}$ is the reconstructred spatial distribution (image) of the chromophore of interest.

In practice, this kind of separation may turn challenging since the exact spectral profile of the background contribution is not always known, e.g. in in-vivo imaging scenario. In addition, the spectral signature of the agent of interest may also be not accurately known, for instance the absorption spectrum may change in different biochemical environments. Moreover, light attenuation and ultrasonic dispersion in tissues leads to a corresponding non-linear relationship between the measured opto-acoustic signals and the corresponding target concentration as a function of depth or target size. This is particularly evident for volumetric tissue imaging since opto-acoustic signals depend on product between local light fluence at different depths and local absorption coefficient of the agent of interest and other background chromophores. Finally, the spectral profile of light propagating in tissue is also altered by depth, since attenuation rate is different depending on wavelength, which may also contribute to intensity variations in the recorded MSOT signals with depth.

These possible issues in spectral unmixing can be tackled by the use of multivariate data analysis and matrix factorization algorithms, such as principal component analysis (PCA), non-negative matrix factorization (NNMF), multivariate curve resolution (MCR) or independent component analysis (ICA). Principal Component Analysis is a blind source unmixing technique, that is based on the assumption that the source components are statistically uncorrelated. PCA yields a linear orthogonal transformation into a new coordinate system, in which the largest data variance is projected onto the first principal component, the largest remaining variance onto the second one, and so on. Consequently, the correlated measurement data is unmixed by being transformed to uncorrelated principal components. PCA can be calculated as a singular value decomposition of M or as an eigenvalue decomposition of its covariance matrix, i.e.

$$R_{PCA} = U_{PCA}^T M, \qquad (6)$$

where U is a transformation matrix that represents absorption spectra of the calculated principal components.

Independent Component Analysis (ICA) is yet another blind source separation technique, but it is based on a different assumption about the sources than PCA. While the latter assumes uncorrelated sources, ICA finds end members that satisfy the more general and therefore stronger condition of statistical independence. The algorithm seeks a transformation of the dependent mixed spectral components into a set of independent source components and also yields the corresponding mixing matrix $U_{ICA}$. Contrary to the pixel-by-pixel processing approach in the differential and fitting unmixing methods, the key element in multivariate approaches is the unaided identification of changes that are common across various pixels, helping to identify contrast agents that have a non-uniform spatial biodistribution.

MSOT allows for a powerful performance in imaging of optical contrast deep within several centimeters of living tissues. This is mainly because it can visualize optical absorption with resolution that is not affected by photon scattering. Instead, optical contrast and markers are visualized with high sensitivity and ultrasonic resolution. Using advanced illumination systems, high frequency detectors, and reconstruction methods, the achieved MSOT imaging quality allows for high-resolution imaging within several millimeters of fully scattering tissue.

BRIEF DESCRIPTION OF DRAWINGS

Further details and advantages of the invention are described in the following with reference to the attached drawings, which show in.

PREFERRED EMBODIMENTS OF THE INVENTION

Embodiments of the inventive system and method are described in the following with particular reference to the provision of the light source device, the light detector device, the optical imaging device and the acoustic detector device relative to the object. Details of operating these components or processing the data collected therewith are not described as far as they are known as such. Several implementations of the invention are foreseen, similar to the existence of multiple optical imaging methods. The embodiments of the invention are illustrated schematically. Accordingly, details like power supply devices, holding devices supporting the object, data interfaces and the like are not shown in the figures.

Figure 1:
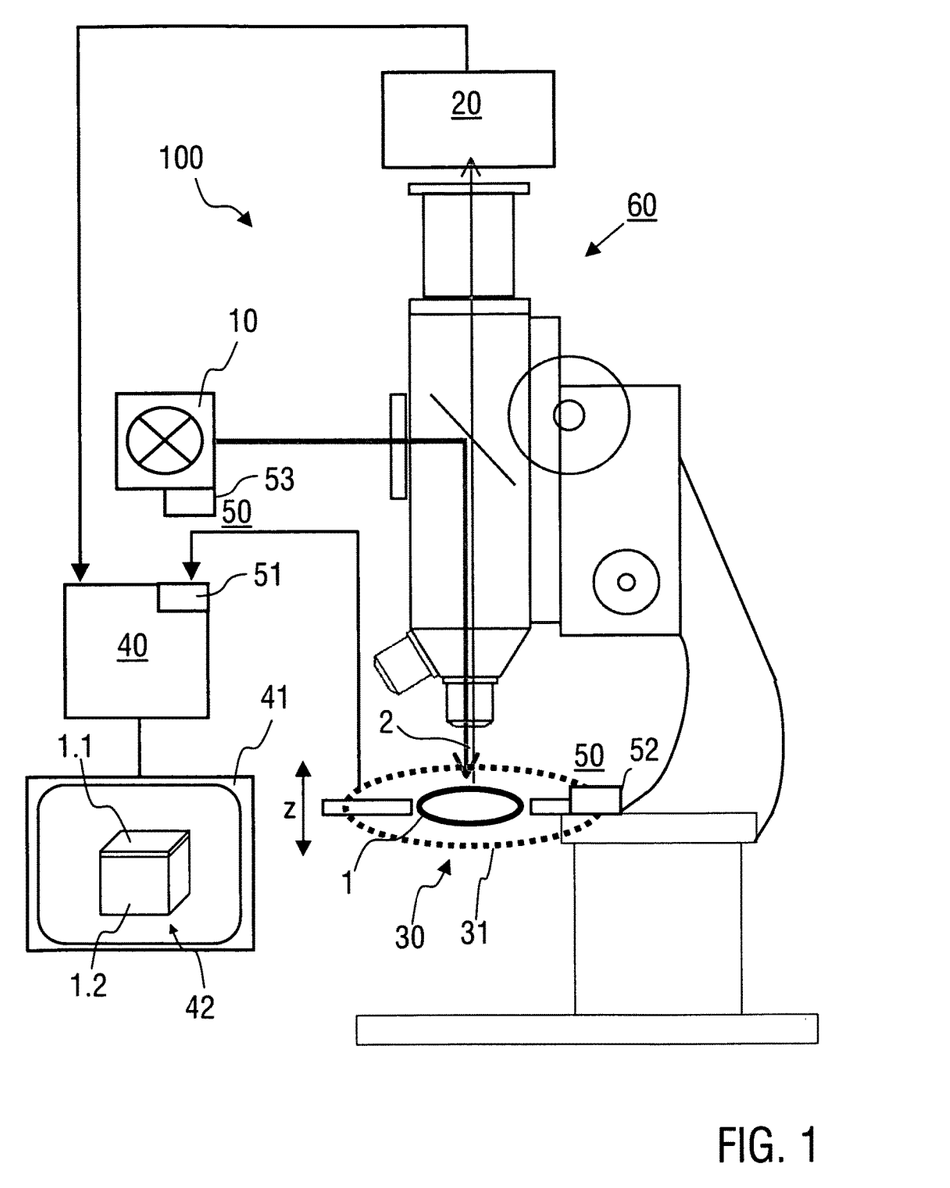
FIG. 1 a schematic illustration of an embodiment of the inventive imaging apparatus.

FIG. 1 shows an embodiment of the inventive hybrid optical/opto-acoustic imaging apparatus 100 which utilizes conventional wide-field illumination arrangement in a vertical axis mode. The imaging apparatus 100 has an optical imaging geometry like an upright or inverted microscope and comprises a light source device 10, a light detector device 20, an acoustic detector device 30, an image reconstruction device 40, a resolution adaptation device 50, and an optical imaging device 60.

The light source device 10 can include two separate light sources, such as a continuous wave and a pulsed nanosecond laser source for the optical and opto-acoustic imaging modes, respectively. Alternatively, the light source device 10 of such a microscope can include one single source only, which is adapted to simultaneously generate efficient optical and opto-acoustic responses in the imaged sample, e.g. by producing intense and short, preferably nanosecond, pulses of light.

In response to a wide-field illumination 2 of an object 1 ("sample"), scattered or fluorescence light emitted by the object 1 is imaged and/or projected by means of the optical imaging device 60 onto the light detector device 20, including photodetectors or a CCD camera, while filters (not shown) can be used for imaging in the fluorescence mode.

Ultrasonic transducers 31 of the acoustic detector device 30 are provided in order to optimally detect the opto-acoustic signals originating from the imaged area of the object 1. Two-dimensional tomographic data can simultaneously be acquired from a certain horizontal plane by surrounding it by an array of multiple transducers 31 which are preferably cylindrically focused onto this plane. Three-dimensional data can again be acquired by translating the array along the vertical z-axis (see arrow). Yet another tomographic arrangement can be considered by placing an array of unfocused detector elements around the imaged area in order to readily capture three-dimensional opto-acoustic datasets. Alternatively, detection can be done using a single planar transducer (not shown), which is rotated in the horizontal x-y plane to acquire tomographic two-dimensional data and is also translated along the vertical z-axis for acquisition of three-dimensional datasets.

The light detector device 20 and the acoustic detector device 30 are coupled with the image reconstruction device 40. The image reconstruction device 40 includes at least one data processor which is adapted to process the signals collected with the light detector device 20 and the acoustic detector device 30 and to create an optical image, an opto-acoustic image and/or a hybrid optical/opto-acoustic image 42, at least one of which being displayed on a display 41. Furthermore, the image reconstruction device 40 includes a control circuit arranged for controlling at least one of the light source device 10, light detector device 20, the acoustic detector device 30 and/or the optical imaging device 60. In the example shown in FIG. 1, the three-dimensional hybrid optical/opto-acoustic image 42 exhibits a thin upper image region corresponding to an optical image of a superficial segment 1.1 or plane of the object 1 with a microscopic optical resolution and a significantly thicker lower image region corresponding to an opto-acoustic image of a considerably deeper segment 1.2 of the object 1 under investigation with a mesoscopic ultrasonic resolution.

Signal processing is provided depending on the particular tomographic arrangement of the ultrasonic transducers 31, wherein the opto-acoustic image reconstruction can optimally be done by, e.g., cylindrical or spherical back-projection, model-based algorithms or opto-acoustic image reconstruction approaches known from prior art. Creating the hybrid image 42 is done by registering the optical and opto-acoustic images.

The imaging apparatus 100 is preferably arranged for simultaneously producing planar microscopic and/or macroscopic optical images and mesoscopic opto-acoustic images of the object 1. Since opto-acoustic signals are generally not affected by photon scattering, opto-acoustic image resolution will be solely determined by the diffraction limit of the ultrasound detection, i.e. by the available bandwidth of the ultrasonic transducers and their spatial characteristics. In case of the wide-field illumination shown in FIG. 1, the optical images will only allow for planar (two-dimensional) imaging capacity without depth resolution.

The resolution adaptation device 50 includes a filtering unit 51 integrated in the image reconstruction device 40. With the filtering unit 51, the collected acoustic signals are subjected to a frequency filtering step selected in dependency on the imaging properties to be obtained. As examples, a Fourier domain filtering or a wavelet-domain filtering are applied which are selected e. g. in dependency on an expected spatial structure and spatial frequencies of interest and/or the intended imaging depth within the object 1. As a further part of the resolution adaptation device 50, FIG. 1 schematically shows a drive unit 52 moving the acoustic detector device 30 relative to the object 1. The drive unit 52 comprises e. g. a piezo-electric drive shifting the acoustic detector device 30 relative to a holder carrying the object 1. By adjusting the distribution of the detector elements 31 and/or the position thereof relative to the object 1, the resolution of the opto-acoustic image can be set. Finally, a light source modulation unit 53 is shown as a further part of the resolution adaptation device 50. The light source modulation unit 53 creates an input modulation of the object illumination.

Figure 2:
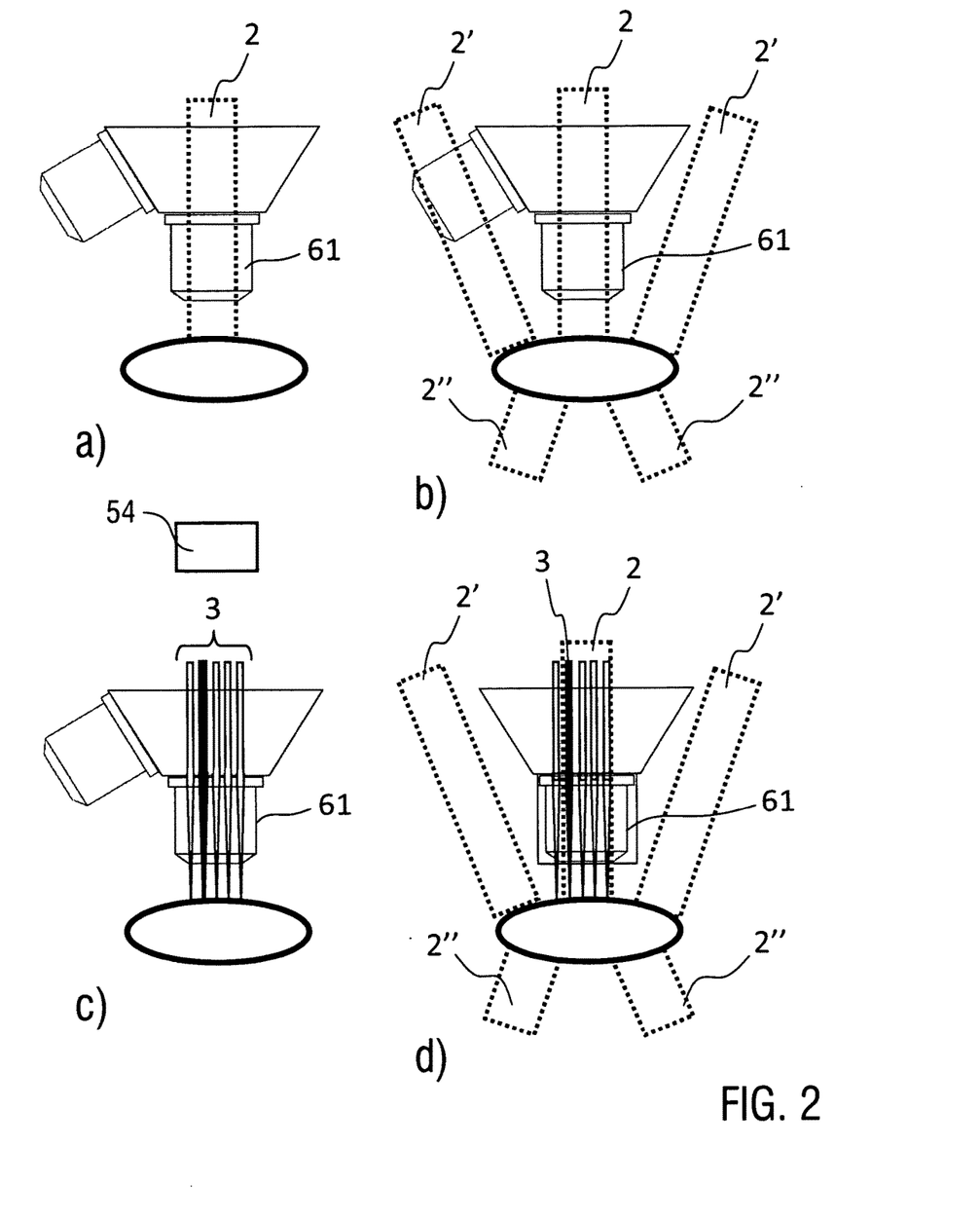
FIG. 2 a schematic illustration of various illumination schemes in the inventive imaging apparatus.

FIG. 2 shows in more detail illumination schemes that can be employed in the inventive system. In particular, wide field illumination 2 can be provided either through the microscope objective 61 (see FIG. 2a) and/or by an illumination 2' and 2" coming from other directions and geometrical arrangements guiding the illumination field past the objective 61 onto the sample (see FIG. 2b), for example using fiber bundles or other optical guidance combinations, or any combination of the two components. Alternatively, a light scanning illumination 3 can be employed for imaging, preferably through the objective 61 (see FIG. 2c) in microscopy and can be further combined with wide filed illumination (see FIG. 2d). The scanning illumination 3 can be created with a light source scanning unit 54 schematically shown in FIG. 2c. The light source scanning unit 54 comprises e. g. a mirror scanner as known from confocal microscopy.

Particularly preferred embodiments of the invention relate to combinations of particular illumination and detection schemes in order to achieve hybrid operation and dynamic resolution adaptation. There are multiple synergistic effects. E.g., light of constant intensity can be combined with light of varying intensity to collect optical and opto-acoustic images in parallel. Light of varying intensity (for example photon pulses) can be combined both for optical and opto-acoustic imaging. By utilizing multiple detectors 31 (like in FIG. 1), the system can increase the sensitivity and signal to noise ratio of the recorded signals even when detecting opto-acoustic responses from the illumination system used for optical microscopy, for example in multi-photon microscopy whereby photon pulses are also employed. In such manner, a conventional or advanced optical microscope can be synergistically employed with an opto-acoustic mesoscope to even lead to improved optical resolution opto-acoustic microscopy. Wide field illumination for achieving opto-acoustic resolution can be instead employed together with laser scanning microscopy, as shown in FIG. 2d.

A particular aspect of the invention is the use of illumination at multiple wavelengths and the corresponding detection of multiple spectra from tissues. This applies in particular to the opto-acoustic method. Whereas the optical methods can detect for example a fluorochrome with single wavelength illumination; by using a filter to cut-off the excitation light, opto-acoustic imaging needs instead to detect the absorption signature of the fluorochrome or any other photo-absorbing agent or nanoparticle. For this reason, capture of opto-acoustic responses in at least two or more wavelengths and the subsequent spectral analysis adds significantly to the application capacity of the hybrid system. The multi-spectral analysis contrast visualized in the optical method can be also visualized in the opto-acoustic method, leading to one more synergistic effect towards achieving hybrid imaging. In this manner, contrast unique to the opto-acoustic method (haemoglobin, melanin, blood vessels) can be combined on an image with optical and opto-acoustic contrast. Similarly, high optical resolution superficial images of a certain contrast can be combined with images of the same contrast obtained from deeper in tissue, as shown in FIG. 1 by means of an exemplary hybrid image 42.

Moreover, light sheet illumination can be also employed by the hybrid system, wherein the object 1 is illuminated with a thin layer, i.e. a sheet or plane, of light. This so-called single-plane illumination approach improves localization and generation of both optical and opto-acoustic signals in the selected particular plane and, by this means, improves signal-to-noise ratio, reduces out-of-plane artifacts and increases imaging speed and image quality.

Further advantageous embodiments of the invention relate to the geometrical adaptation or arrangement of the ultrasonic detectors employed to the illumination pattern considered. Since the illumination pattern of the hybrid system may vary to adapt to different imaging needs, so can the geometrical arrangement of the detectors. Detectors are typically located in arrangements that are larger than the dimensions of the object imaged. A secondary criterion of arrangement is that there should be detectors that offer a view that has a contribution parallel to the illumination plane. In a simplified version the hybrid imaging system may offer only one or a limited number of illumination schemes and a corresponding fixed geometrical arrangement of detectors. In this approach, nevertheless, the ultrasonic detectors are arranged to optimally capture the opto-acoustic signals originating from the illuminated volume (layer) of the tissue. This can be done by scanning a single detector around the object in order to collect tomographic information from the imaged plane or, alternatively, by rotating the object 1 around the imaging plane. Stationary detection can be also done by placing an array of detectors around the imaging plane, which will simultaneously detect the generated opto-acoustic waveforms from multiple projections. In order to maximize the detected pressure variations of the generated acoustic signals and optimally reject out-of-plane artifacts, said array may consist of cylindrically-shaped detectors, focused onto the common imaging plane.

Two-dimensional opto-acoustic image reconstruction can be done using the image processing device 40 by means of cylindrical Radon (back-projection), model-based algorithms or other opto-acoustic image reconstruction approaches. In a preferred embodiment, an array of detectors will be scanned in preferred arrangements around the object to parallelize the detection of signals while offering multiple spatially resolved measurements.

Figure 3:
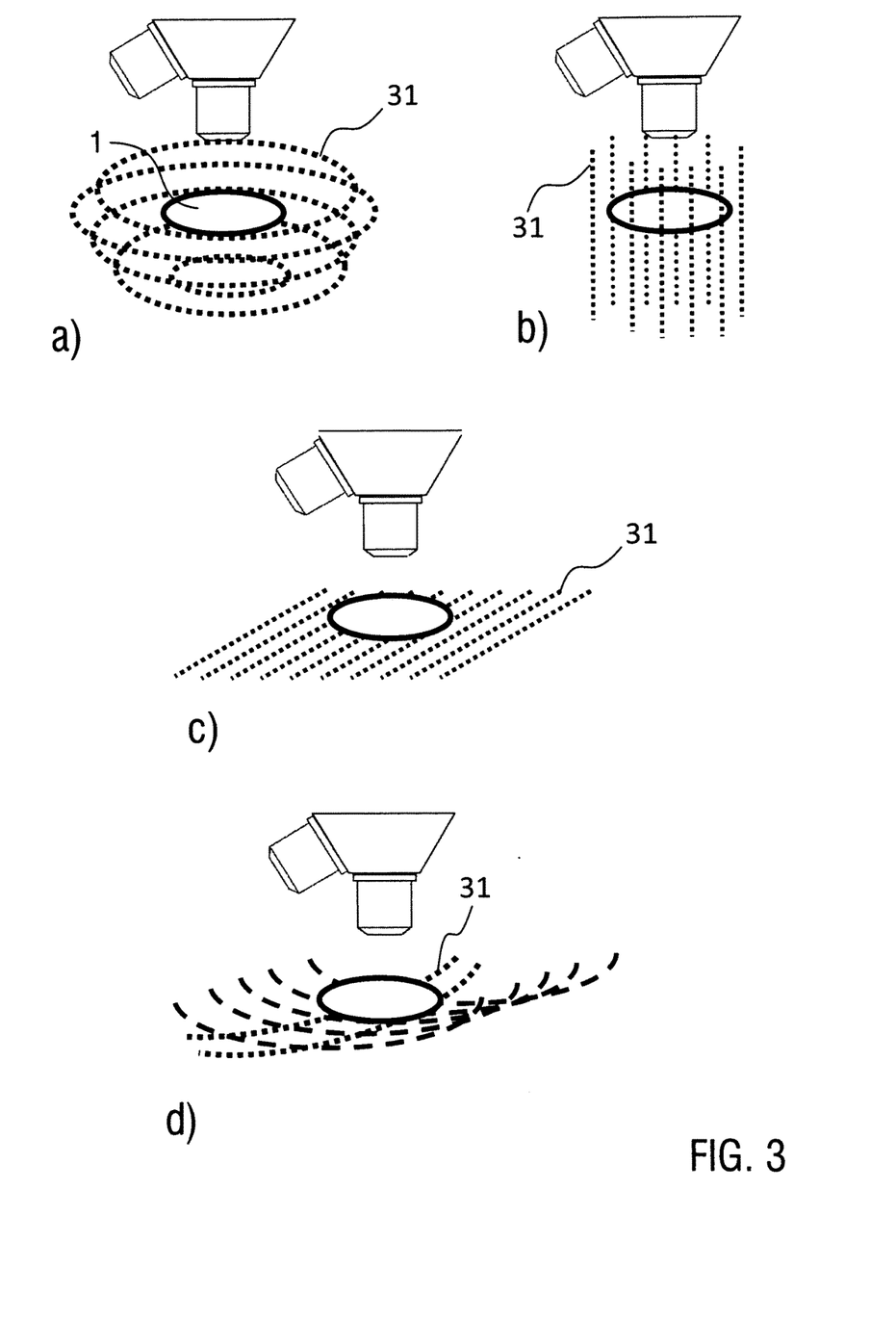
FIG. 3 a schematic illustration of various ultrasonic transducer arrangements in the inventive imaging apparatus.

Examples for scanning detectors by following a two-dimensional or a three-dimensional plane are shown in FIG. 3. FIG. 3a shows an arrangement of dot-like detectors elements 31 around the object 1 ("sample"). Such a pattern can be achieved by scanning a single detector, although in a preferred embodiment an array, e.g. a ring-shaped array, of detector elements 31 is scanned relative to the sample. Such an array of detector elements 31 can be arranged along a curved line so that when scanned, the detector elements 31 can optimally see the object from multiple projections.

FIG. 3b shows the scanning of a vertically oriented linear array of detector elements 31 which can be employed to scan around the object. The detector elements 31 are arranged in along straight lines in parallel to an optical axis of illumination. The scanning pattern could be a simple rotational pattern, like a cylinder as shown, or more complex in nature.

FIG. 3c shows a third detector placement array that can lead to very practical implementations. Herein, the detector or detector array populates a two-dimensional grid of detector elements 31. An even more potent alternative is shown in part FIG. 3d, wherein several features of the inventive hybrid system are simultaneously implemented such as i) a dense grid, ii) projections with parallel contributions to diverse illumination fields and iii) no obstruction of the illumination field by the acoustic detector elements 31. This arrangement, wherein detector array comprises a curved, cup shaped grid of detector elements, can also lead to optimal placement systems. Real-time implementations can be achieved when entire ultrasonic arrays can be employed for parallel detection which could be beneficial in detecting dynamic effects or fast circulating agents.

Figure 4:
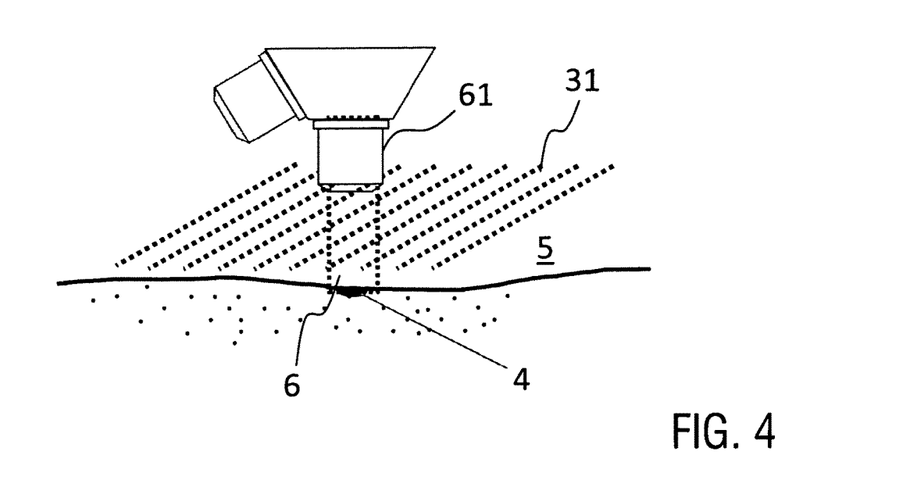
FIG. 4 a schematic illustration of an embodiment of the inventive imaging apparatus in an "epi-illumination" mode appropriate for clinical imaging (skin, other tissues) or imaging of large biological samples and animals.

While the scanning geometries represented in FIG. 3 mainly show detectors that are placed around or at the bottom of the object, similar scanning arrangements can be also implemented from the same side of the illumination by implementing an "epi-illumination" mode shown in FIG. 4. According to the embodiment shown in FIG. 4, the objective 61 of the microscope is placed in a certain distance above a lesion 4 of the skin. Preferably, between the skin and the objective 61 a matching medium 5 for an optical and/or acoustical matching of the components is provided. In the matching medium and between the skin and the objective 61 an array of multiple acoustic detector elements 31 is provided which can be stationary or moveable relative to the skin. This embodiment is in analogy to an upright microscope and can be very advantageous when imaging parts of large tissues, such as clinical imaging in humans or animals (mice, rats, other) or larger biological specimen (excised tissues, food items etc).

In this case, scanning can be arranged around an illumination beam 6 that can be either wide-filed or light scanning. Correspondingly, an optical microscopy image can be complemented by an opto-acoustic image allowing penetration deeper in tissue. This is particularly useful, for example, in skin cancer imaging whereby the penetration of optical microscopy alone does not suffice to visualize the penetration and the architectural or function and molecular appearance of a lesion deeper than a few hundred microns.

Figure 6:
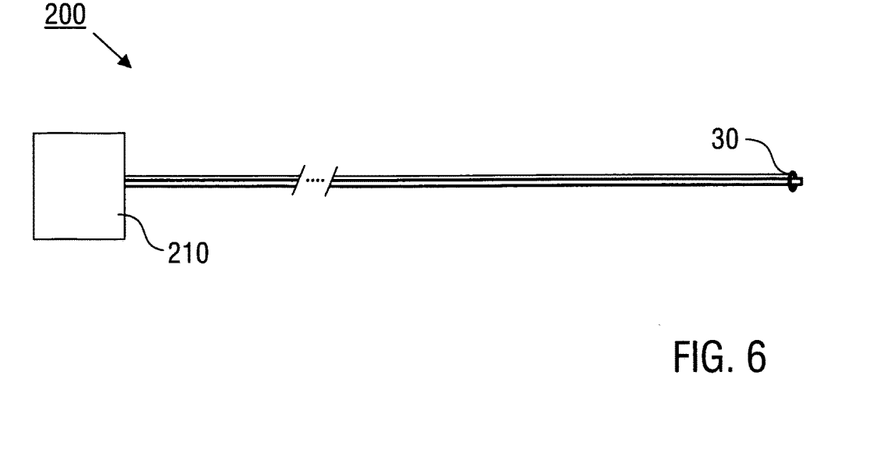
FIG. 6 a schematic illustration of an endoscope device adapted for hybrid imaging according to the invention.
Figure 7:
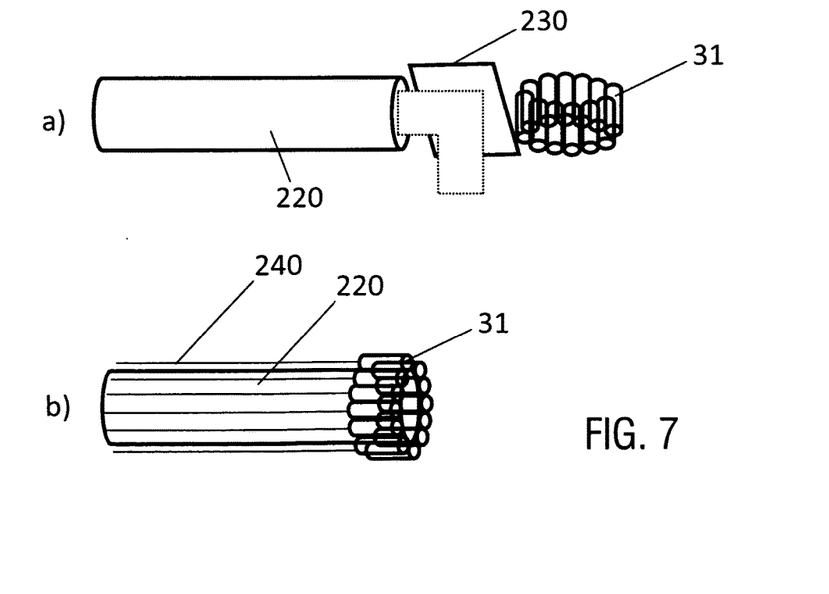
FIG. 7 a schematic illustration of two embodiments of the distal end of an endoscope device adapted for hybrid imaging according to the invention.

This embodiment of the invention provides a particularly advantageous solution wherein the lesion can be visualized with a typical high-resolution optical method (photographic or tissue-sectioning) and complemented then by a three-dimensional vision of the lesion characteristics. In melanomas or dark lesions, the use of wide beam illumination for opto-acoustic imaging can circumvent significant problems of light attenuation by conventional optical methods, since tissue scattering allows illumination of the entire lesion, even deep seated parts, which is not typically available when coherent or highly focused light is required for image formation such as in the case of optical methods including multi-photon microscopy or optical coherence tomography. Other possible applications are oral cancers, peripheral arterial disease, oxygenation measurements by multi-spectral methods. This concept can be also implemented endoscopically, as shown in FIGS. 6 and 7 discussed in detail below.

A further aspect of the present invention is to consider the particularities of optical properties of the sample scanned. If the object does not scatter light, i.e. in case of naturally transparent or chemically treated non-diffusive specimen, the scattered or fluorescent light can be readily collected from the imaged plane by placing a CCD camera in the orthogonal direction. Subsequently, a high resolution optical image can be formed. Three-dimensional imaging then needs to consider explicit scanning of illumination throughout the sample, so that opto-acoustic responses are generated from the entire sample. This can be achieved by using photon diffusers or by translating an illumination plane, together with the ultrasonic transducer/s (detector elements 31), along the vertical axis.

Instead, if the imaged object scatters photons, the impinging light will be diffused through the sample. In this case, illumination requirements can be simplified, however image reconstruction approaches will change. Since the spatial resolution in opto-acoustic imaging is generally not affected by light scattering in the object, the opto-acoustic signal collection and image reconstruction can be done in a similar fashion. However, the generated opto-acoustic signal strength is generally proportional to the light fluence. Thus, images would still have to be corrected if significant light scattering and/or attenuation exists in the sample. The correction might be done by modelling light distribution in tissue using Monte-Carlo, light diffusion or photon transport equations, while considering the correct illumination pattern on the surface of the imaged object, whose boundaries can be readily captured by the camera. More advanced methods for extracting the light fluence distribution can also be applied, such as the sparse image representation approaches, which calculate the light fluence based on blind decomposition of raw opto-acoustic images without prior knowledge on the optical properties of the imaged object or the particular illumination and measurement geometries. The optical imaging approach in case of scattering objects might also significantly change, as generation of scattered or fluorescence light is not confined anymore to a focal point or thin plane, which causes significant deterioration in spatial localization, depth resolution and the overall volumetric imaging capacity. Consequently, modelling of light propagation (diffusion) in tissue would also be essential in order to at least partially restore spatial resolution loss of the optical images due to scattering. Furthermore, in order to improve volumetric visualization capabilities, broader tomographic collection of the scattered radiation will be further necessary. This can be again done by translating the illumination plane, together with the ultrasonic transducer/s, along the vertical axis.

Figure 5:
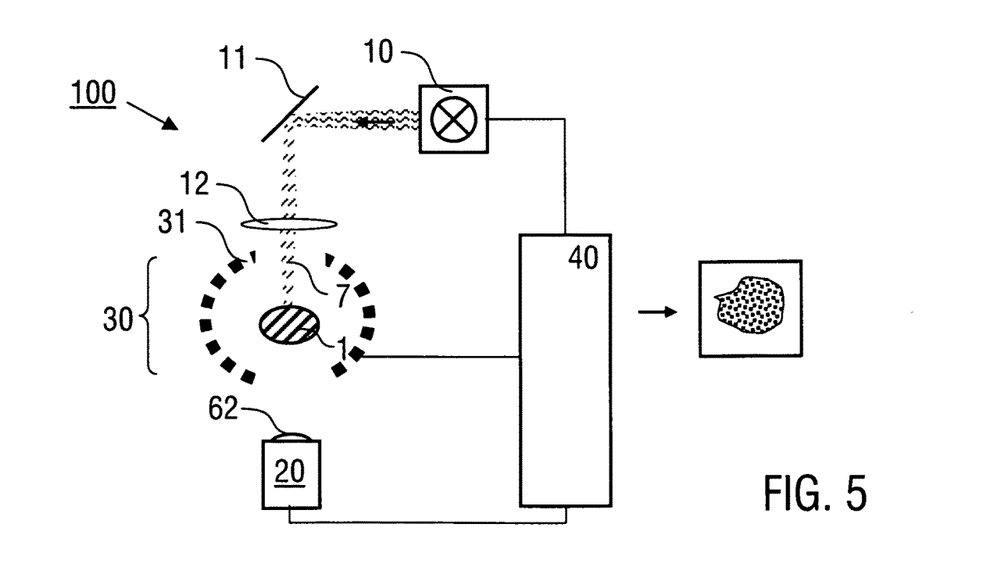
FIG. 5 a schematic illustration of a further embodiment of the inventive imaging apparatus.

FIG. 5 shows another embodiment of the inventive hybrid imaging system 100 and method involving illuminating the imaged object 1 by a focused pencil beam 7. The pencil beam 7 is formed by deflecting light from the light source device 10 via a plane mirror 11 and a focussing lens 12 to the object 1. At least one of the light source device 10 and a holder (not shown) of the object 1 can be moved for scanning the pencil beam 7 on the object 1. Similarly, a number of optical components for guiding light can be employed to guide light around the object. Light emitted by the object 1 is projected and/or focused by a lens 62 or lenses onto a light sensitive surface of the light detector device 20.

In some cases this is preferred in order to improve spatial resolution of optical imaging in the presence of scattering in the imaged object 1. For instance, tomographic reconstruction of optical coefficients (scattering, absorption) or fluorescence distribution can be done by point illumination and detection of light intensity at the surface of optically diffusive object 1. In this way, multiple points on the tissue boundary are illuminated in a time-sharing fashion and diffuse light patterns are collected around the boundary using the light detector device 20 including photodetector sets or a CCD camera. Each source-detector pair effectively implements a different projection through the tissue, albeit following diffusive propagation patterns. Fluorescence measurements can be obtained using appropriate filters in front of the detectors, although the same generic tomographic principles are used for reconstruction of intrinsic tissue contrast, that is, absorption or scattering. These measurements are then combined in a tomographic scheme, which can be written as a system of equations that are solved for the unknown, spatially dependent fluorochrome concentration. This generic mainframe, combined with appropriate fluorescent molecules with specificity to cellular and subcellular processes, forms the basis of fluorescence molecular tomography (FMT), a technology directed towards noninvasive quantitative whole-body molecular imaging. Opto-acoustic signal acquisition and image reconstruction can in this case be done in the two- or three-dimensional tomographic fashion, similarly to the previous embodiments. Yet, accurate correction for light distribution in the imaged volume will be even more crucial for the point illumination approach, since the light intensity declines abruptly as the photons diffuse from the focal point on the surface into the scattering volume.

Further hybrid image reconstruction methods are also possible, where the imaging data acquired by one modality can be combined into the image formation process of the other modality in order to improve the outcome. For example, the optical absorption data, acquired by the opto-acoustic modality, can be used to improve quantification of the images by more accurate modelling of light propagation in tissues, information that can be incorporated into tomographic reconstruction of the optical signals by e.g. introducing corrections for light attenuation in the inverse procedure of FMT.

FIG. 6 schematically shows an embodiment of the invention where an endoscope device 200 is provided with the hybrid imaging apparatus. In a basis unit 210 of the endoscope device 200, the light source device, the light detector device, the optical imaging device and the image reconstruction device are arranged. The acoustic detector device 30, comprising a circular array of transducers, is arranged at a distal end of the endoscope device 200.

The endoscopic device 200 can be similarly employed to offer an optical resolution and an opto-acoustic resolution image. The optical image can also be used to guide the opto-acoustic image. For example a wide field optical endoscope can be combined with an opto-acoustic sensing system. Alternatively, similarly to the previous description, a confocal or two-photon microscope can be employed together with the opto-acoustic imaging system.

Details of preferred embodiments of the distal end of the endoscope device 200 are shown in FIG. 7. According to FIG. 7a, a deflection mirror 230 is provided near the distal end face of a light guide 220 for deflecting an illumination light beam emerging from the end face of the light guide 220 onto the tissue to be investigated. Additionally, acoustic detector elements 31 are provided which are directed essentially in parallel to the deflected illumination light beam so that they can reliably detect acoustic signals generated in the illuminated tissue. According to FIG. 7b, light emerging from the distal end face of the light guide 220 is not deflected and can impinge directly onto the tissue under investigation. Accordingly, the circular array of acoustic detectors 31 can be easily arranged around the end part of the light guide and can, in this way, reliably detect acoustic signals generated in the tissue. At an outer surface of the light guide 220 electric cables 240 are provided for guiding electrical signals produced by the acoustic detectors 31 when detecting acoustic waves along the light guide 220 to the image processing device arranged in the basis unit 210 (see FIG. 6).

The embodiments described above find multiple applications in various fields of biology and medicine, both in research and clinical healthcare. Cancer research, drug discovery, developmental biology, tissue engineering but also clinical diagnosis, theranostics and therapy follow up can be enabled with this approach. By allowing penetration deeper in tissue, in fact the proposed system can enable applications in all fields whereby optical microscopy and optical endoscopy is employed. In skin or gastro-intestinal cancer the proposed system can be employed to bring more accurate interrogation of the disease and the investigation of drugs. In diagnostic applications, the proposed method can be employed to detect blood or tissue constituents in-vivo with high resolution and penetration depth. Three-dimensional scaffolds can also be visualized in several biotechnology applications whereby the technique can also image foods and materials combining the conventional optical views with deep-penetrating opto-acoustic methods.

The features of the invention disclosed in the above description, the drawings and the claims can be of significance both individually as well as in combination for the realisation of the invention in its various embodiments.

The invention claimed is:

1. An imaging apparatus for imaging a biological object under investigation, comprising:
    a light source device arranged for an illumination of the object,
    a light detector device arranged for detection of light emitted by the object in response to the illumination of the object,
    an acoustic detector device arranged for collecting acoustic signals at multiple frequencies, generated in the object in response to the illumination of the object, the acoustic detector device having a frequency response wherein the acoustic detector device produces signals that depend on the frequencies of the collected acoustic signals,
    an image reconstruction device arranged for reconstructing an optical image of the object having a first resolution and an opto-acoustic image of the object having a second resolution,
    a resolution adaptation device configured to adjust imaging properties of the opto-acoustic image, said imaging properties including at least one of the second resolution and an imaging depth of the opto-acoustic image, wherein the second resolution of the opto-acoustic image is adjusted by at least one of the following: adapting the frequency response with the imaging depth and subjecting the collected acoustic signals to at least one frequency filtering in dependency on the imaging depth, and
    the image reconstruction device is further arranged for combining the optical image and the opto-acoustic image into a hybrid optical/opto-acoustic image wherein the first resolution is gradually exchanged for the second resolution at increasing imaging depths to obtain a hybrid optical/opto-acoustic image of varying resolution with imaging depth.

2. The imaging apparatus according to claim 1, wherein: the resolution adaptation device is arranged for adjusting the imaging properties of the opto-acoustic image in dependency on optical, acoustic and/or geometric properties of the object or parts thereof.

3. The imaging apparatus according to claim 1, wherein: the resolution adaptation device includes a filtering unit arranged for subjecting the collected acoustic signals to the at least one frequency filtering in dependency on the imaging depth, wherein acoustic signals having high frequencies in the range from 30 MHz to 60 MHz are transmitted to the image reconstruction device or acoustic signals having low frequencies in the range from 5 MHz to 10 MHz are transmitted to the image reconstruction device, depending on the imaging depth.

4. The imaging apparatus according to claim 1, wherein: the resolution adaptation device includes a drive unit being arranged for moving the acoustic detector device or parts thereof relative to the object.

5. The imaging apparatus according to claim 4, wherein: the acoustic detector device comprises at least one detector element being movable relative to the object, and the drive unit is arranged for moving the at least one detector element along a linear or curved, in particular a circular line, and/or along a planar or curved surface.

6. The imaging apparatus according to claim 1, wherein: the resolution adaptation device includes a light source modulation unit arranged for subjecting the illumination of the object to a predetermined input modulation selected in dependency on the imaging properties of the opto-acoustic image to be obtained.

7. The imaging apparatus according to claim 1, wherein: the acoustic detector device is arranged for collecting the acoustic signals along a plurality of angular projection directions through the object.

8. The imaging apparatus according to claim 7, wherein: the acoustic detector device comprises a detector array with multiple detector elements being distributed in proximity to the object.

9. The imaging apparatus according to claim 8, wherein the multiple detector elements are located on:
    at least one of a linear or curved line or a planar or curved surface around the object.

10. The imaging apparatus according to claim 1, wherein the acoustic detector device comprises at least one of:
    at least one unfocused detector element which obtains volumetric opto-acoustic image information of the object, and
    at least one focused detector element which obtains opto-acoustic image information simultaneously from locations on a line or plane on or within the object.

11. The imaging apparatus according to claim 1, wherein the image reconstruction device is arranged for reconstructing:
    the optical image representing a surface segment of the object, and
    the opto-acoustic image representing a volume segment of the object.

12. The imaging apparatus according to claim 11, wherein the image reconstruction device is arranged for reconstructing:
    the opto-acoustic image representing both the surface segment and the volume segment of the object.

13. The imaging apparatus according to claim 1, wherein the light source device is adapted for at least one of:
    a wide-field illumination of the object,
    a patterned illumination of the object,
    a single plane illumination of the object,
    a focused illumination of the object,
    a pencil-beam illumination of the object,
    an illumination of the object with a varying light intensity, or
    an illumination of the object at two or more different wavelengths.

14. The imaging apparatus according to claim 1, wherein the light source device includes at least one of:
    a light-emitting diode,
    a laser diode, and
    a pulse laser source.

15. The imaging apparatus according to claim 14, wherein:
    the pulse laser source is adapted for a multi-photon absorption in the object.

16. The imaging apparatus according to claim 1, wherein: an imaging device is arranged for projecting the light emitted by the object onto the light detector device.

17. The imaging apparatus according to claim 16, wherein:
said imaging device comprises a confocal and/or multi-photon laser scanning microscope.

18. The imaging apparatus according to claim 1, wherein:
the light source device, the light detector device and the acoustic detector device are coupled with an endoscope device.

19. The imaging apparatus according to claim 18, wherein:
the acoustic detector device is arranged on a distal portion of the endoscope device.

20. A method for imaging an object under investigation, comprising the steps of:

illuminating of the object with a light source device, detecting light emitted by the object in response to the illumination of the object with a light detector device, collecting acoustic signals at multiple frequencies generated in the object in response to the illumination of the object with an acoustic detector device, the acoustic detector device having a frequency response wherein the acoustic detector device produces signals that depend on the frequencies of the collected acoustic signals, reconstructing an optical image of the object having a first resolution and an opto-acoustic image of the object having a second resolution with an image reconstruction device, and adjusting imaging properties of the opto-acoustic image with a resolution adaptation device, said imaging properties including at least one of the second resolution and an imaging depth of the opto-acoustic image, wherein the second resolution of the opto-acoustic image is adjusted by at least one of adapting the frequency response with the imaging depth and subjecting the collected acoustic signals to at least one frequency filtering in dependency on the imaging depth, combining the optical image and the opto-acoustic image into a hybrid optical/opto-acoustic image wherein the first resolution is gradually exchanged for the second resolution at increasing imaging depths to obtain a hybrid optical/opto-acoustic image of varying resolution with imaging depth.

* * * * *

UNITED STATES PATENT AND TRADEMARK OFFICE
CERTIFICATE OF CORRECTION

PATENT NO. : 9,964,747 B2  
APPLICATION NO. : 14/406654  
DATED : May 8, 2018  
INVENTOR(S) : Vasilis Ntziachristos et al.

Page 1 of 1

It is certified that error appears in the above-identified patent and that said Letters Patent is hereby corrected as shown below:

In the Specification

Column 5, Line 40 delete ". . . allows to accomodate . . ." and insert --. . . allows to accommodate . . .--

Column 6, Line 39 delete ". . . in particular a circular line, and/or . . ." and insert --. . . in particular a circular, line and/or . . .--

Column 6, Line 57 delete ". . . sin-like . . ." and insert --. . . sine-like . . .--

Column 8, Line 19 delete ". . . manner be distributed . . ." and insert --. . . manner distributed . . .--

Column 12, Line 52 delete ". . . generalized into a more realistic . . ." and insert --. . . generalized into more realistic . . .--

Column 14, Line 60 delete ". . . the reconstructred spatial distribution . . ." and insert --. . . the reconstructed spatial distribution . . .--

Signed and Sealed this  
Tenth Day of July, 2018

Andrei Iancu  
*Director of the United States Patent and Trademark Office*